United States Patent
Kohara

(10) Patent No.: US 7,759,400 B2
(45) Date of Patent: Jul. 20, 2010

(54) PRESSURE-SENSITIVE ADHESIVE COMPOSITION AND SKIN PATCH

(75) Inventor: Minoru Kohara, Kyoto (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 675 days.

(21) Appl. No.: 10/584,372

(22) PCT Filed: Jan. 7, 2005

(86) PCT No.: PCT/JP2005/000104

§ 371 (c)(1),
(2), (4) Date: Oct. 26, 2006

(87) PCT Pub. No.: WO2005/066268

PCT Pub. Date: Jul. 21, 2005

(65) Prior Publication Data

US 2008/0032127 A1 Feb. 7, 2008

(51) Int. Cl.
*A61F 13/02* (2006.01)
*C08F 220/20* (2006.01)
*C08F 220/06* (2006.01)

(52) U.S. Cl. ............... 514/772.4; 525/328.8; 525/329.7; 514/772.6; 514/772.5; 524/560

(58) Field of Classification Search ................. 524/560; 525/328.8, 329.7; 514/772.4, 772.5, 772.6
See application file for complete search history.

(56) References Cited

U.S. PATENT DOCUMENTS

| | | | |
|---|---|---|---|
| 4,066,592 A | 1/1978 | Wismer et al. | |
| 5,049,417 A * | 9/1991 | Tsubota et al. | 427/208.6 |
| 5,391,406 A | 2/1995 | Ramharack et al. | |
| 5,851,662 A * | 12/1998 | Suzuki et al. | 428/352 |
| 6,146,656 A * | 11/2000 | Hori et al. | 424/448 |
| 6,558,790 B1 * | 5/2003 | Holguin et al. | 428/355 R |
| 6,632,906 B1 * | 10/2003 | Kamiyama | 526/316 |
| 7,034,083 B2 * | 4/2006 | Yasukochi et al. | 525/337 |

FOREIGN PATENT DOCUMENTS

| | | |
|---|---|---|
| EP | 1369112 A1 | 12/2003 |
| GB | 2213157 A | 8/1989 |
| JP | 03-220120 | 9/1991 |
| JP | 05-247416 | 9/1993 |
| JP | 06-023029 | 2/1994 |
| JP | 09-137143 | 5/1997 |
| JP | 09-217040 | 8/1997 |
| JP | 2003-213222 | 7/2003 |
| JP | 2004-035533 | 2/2004 |
| WO | WO 00/44846 | 8/2000 |
| WO | WO 03062342 A1 * | 7/2003 |

* cited by examiner

*Primary Examiner*—Satya B Sastri
(74) *Attorney, Agent, or Firm*—Licata & Tyrrell P.C.

(57) ABSTRACT

It is intended to provide a composition which has well-balanced pressure-sensitive adhesiveness and cohesive force as well as favorable application properties to the skin, and a patch which has the above-described characteristics and hardly peels off. This object can be achieved by providing a composition comprising an acrylic copolymer containing from 3 to 25% by weight of hydroxyethyl (meth)acrylate as a constituent, a plasticizer and a pseudo-crosslinking compound, wherein the ratio of the content of the plasticizer to the content of the pseudo-crosslinking compound ranges from 30:1 to 250:1, and a patch.

14 Claims, 1 Drawing Sheet

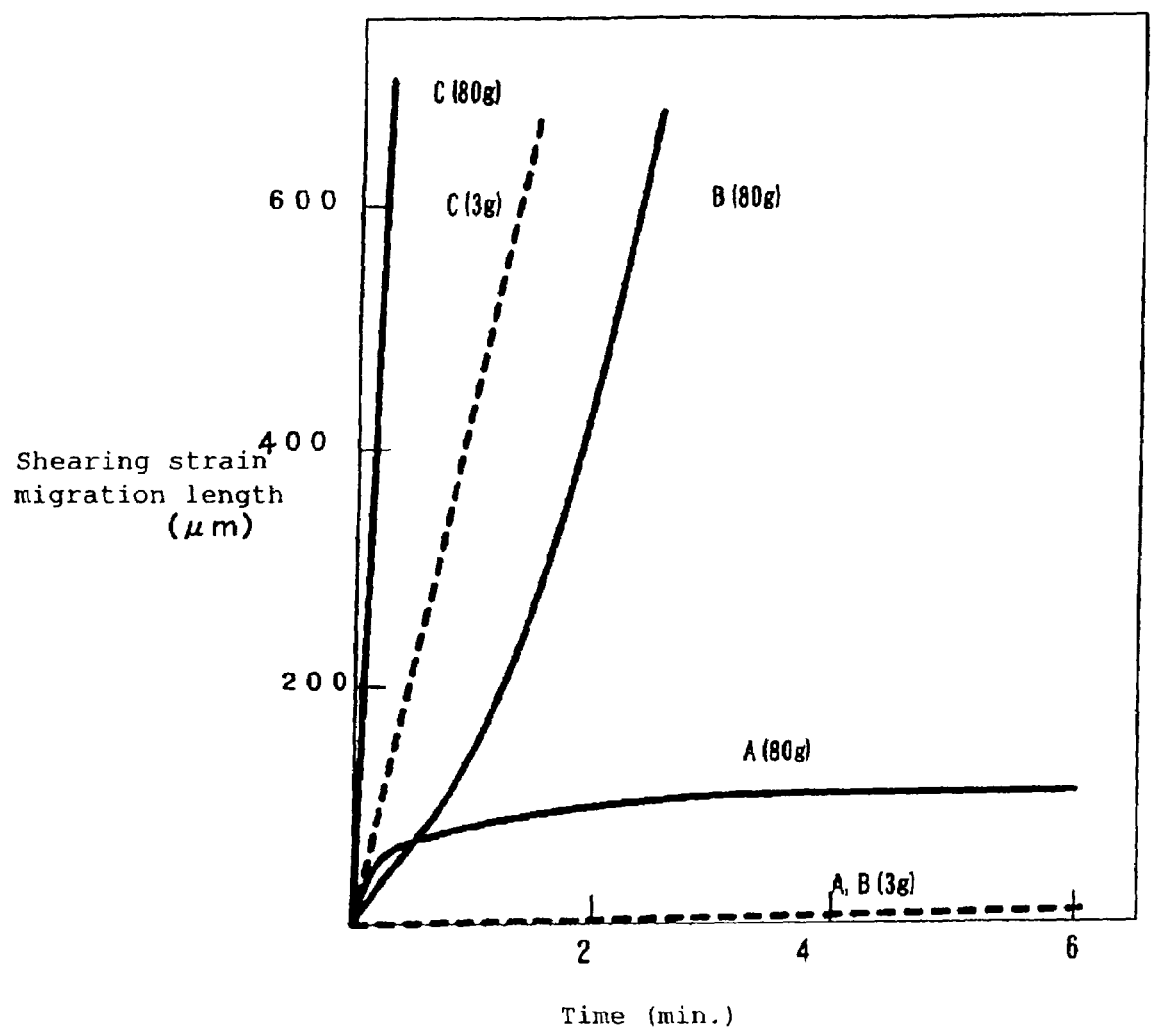
[Figure 1]

PRESSURE-SENSITIVE ADHESIVE COMPOSITION AND SKIN PATCH

This patent application is the National Stage of International Application No. PCT/JP2005/000104, filed Jan. 7, 2005, which claims the benefit of priority from Japanese Application No. 2004-002491, filed Jan. 7, 2004 each of which are herein incorporated by reference in their entirety.

TECHNICAL FIELD

The invention relates to a composition which is excellent in a pressure-sensitive adhesiveness property (pressure-sensitive adhesiveness) and a cohesive property and low in an irritation property and a patch for a medical use, a cosmetic use and the like.

BACKGROUND ART

Although conventionally, the therapy of a disease was generally made by an oral administration or parenteral administration of a drug was general, relatively recently a method to transdermally administer a drug into the body has been used. As a characteristic of a transdermal absorption preparation, it adheres closely for 24 to 48 hours in general, whereby absorption of a designated amount of a drug is necessary, and it is necessary that it adheres closely and does not peel off even when sweating or having a bath. In addition, it is also necessary that it can be peeled off with a peeling force in such a degree as not to be painful when peeling off, and if a pressure-sensitive adhesiveness is strong beyond necessity, hair plucking or keratin peeling occur when peeling off, while a mechanistic skin irritation due to pulling of the skin is produced. As the results, erythema occurs and in a severe case incrustation or edema formation are accompanied, whereby these last for several days after peeling off; and therefore, it is necessary to minimize these inconveniences as much as possible. In addition, it is also necessary not to let a pressure-sensitive adhesive agent remain on a skin surface after peeling off a transdermal absorption preparation from the skin.

Many of acrylic pressure-sensitive adhesive agents themselves at present have appropriate adhesive physical-properties and do not spoil the adhesive physical-properties even letting a small amount of drug be contained in them at a solubilized or crystalline states. However, although a transdermal absorption preparation using this pressure-sensitive adhesive agent has the above characteristics, there was a defect that in case of adding a large amount of a softener, a plasticizer or the like in order to improve a drug release, a cohesive force was insufficient and a glue residue occurred. Therefore, in order to get a excellent patch it is necessary to solve in particular the problem of the glue residue.

In a transdermal absorption preparation, a method to crosslink a pressure-sensitive adhesive agent has been used in order to secure an appropriate cohesive force of a pressure-sensitive adhesive layer and to remove a glue residue. For example, a method to micro crosslink the pressure-sensitive adhesive agent itself by a crosslinking agent and the like, a method to crosslink by a metal ion crosslinking, a urethane crosslinking, an epoxy crosslinking, a melamine crosslinking or a radical reaction by a peroxide compound or an electron beam irradiation is known. However, when applying such an above crosslinking method, the cohesive force was improved; however, the pressure-sensitive adhesive property was lowered due to hardening of the pressure-sensitive adhesive agent and there was a defect that a sticking property became poor.

In addition, as improvement of the above crosslinking pressure-sensitive adhesive agent is proposed a crosslinking method to let a large amount of a plasticizer (e.g. Patent documents 1 and 2) be contained. However, although in the case of this transdermal absorption preparation a shape keeping property of the pressure-sensitive adhesive layer could be raised, it had defects that a preparation design was difficult in which a pressure-sensitive adhesiveness to the skin and a cohesive force of the pressure-sensitive adhesive agent were balanced, and a drug stability was apt to become worse due to reaction of a crosslinking agent and a drug, and so on.

In addition, an adhesive agent and a pressure-sensitive adhesive preparation aiming a moderate combination of a pressure-sensitive adhesive property and a cohesive property are known (Patent document 3). However, in such a pressure-sensitive adhesive agent and a pressure-sensitive adhesive preparation, a skin sticking property, that is, a follow-up property is not necessarily sufficient.

Patent document 1: JP, B, 2700835
Patent document 2: JP, B, 3014188
Patent document 3: JP, A, 2003-213222

DISCLOSURE OF THE INVENTION

Problem to Be Solved by the Invention

The invention is intended to provide a composition which has well-balanced pressure-sensitive adhesiveness and cohesive force as well as favorable application properties to the skin, and a patch which has these physical properties and hardly peels off.

Means for Solving Problem

During extensive research considering the above problems, the inventors surprisingly found out that the above problems are solved by making an acrylic copolymer which makes a specific amount of hydroxyethyl (meth)acrylate as a constituent, a pseudo-crosslinking compound and a plasticizer as essential constituents and further by changing those contents, and accomplished the invention by further investigation.

Namely, the invention relates to a composition comprising an acrylic copolymer containing from 3 to 25% by weight of hydroxyethyl (meth)acrylate as a constituent, a plasticizer and a pseudo-crosslinking compound, wherein the ratio of the content of the plasticizer to the content of the pseudo-crosslinking compound ranges from 30:1 to 250:1.

In addition, the invention relates to the above composition, wherein a content of the plasticizer is from 30 to 200 parts by weight relative to 100 parts by weight of an acrylic copolymer.

Further, the invention relates to the above composition, wherein a content of the pseudo-crosslinking compound is from 0.3 to 10 parts by weight relative to 100 parts by weight of the acrylic copolymer.

Furthermore, the invention relates to the above pressure-sensitive adhesive composition, wherein the acrylic copolymer is a copolymer comprising one or more from alkyl (meth) acrylate, hydroxyethyl (meth)acrylate and N-vinyl-2-pyrrolidone.

In addition, the invention relates to the above pressure-sensitive adhesive composition, wherein the alkyl (meth)acrylate is one or more consisting of an alcohol ester with an alkyl group of carbon numbers 4-12, a content thereof being from 30 to 80% by weight based on the entire copolymer, a content of hydroxyethyl (meth)acrylate is from 3 to 25% by weight based on the entire copolymer, and a content of N-vinyl-2-pyrrolidone is from 5 to 25% by weight based on the entire copolymer.

In addition, the invention relates to the above composition, wherein a shearing strain migration length (3 g, 2 min.) of a pressure-sensitive adhesive layer containing the composition is not more than a thickness of the pressure-sensitive adhesive layer, and a shearing strain migration length (80 g, 5 min.) is not less than 10 times of a thickness of a pressure-sensitive adhesive layer.

Further, the invention relates to the above composition, wherein the pseudo-crosslinking compound is one or more from boric acid and/or a salt thereof, an amine compound, an aluminate and a phenol compound.

In addition, the invention relates to a patch comprising a pressure-sensitive adhesive layer comprising any of the above-described pressure-sensitive adhesive compositions, and a backing.

Further, the invention relates to the above patch comprising a skin valuable.

And, the invention relates to the above patch, wherein the skin valuable is a drug and/or a cosmetic material.

By making an acrylic copolymer (containing from 3 to 25% by weight of hydroxyethyl (meth)acrylate in copolymers), a plasticizer and a pseudo-crosslinking compound as essential components, and by making the ratio of the content of the plasticizer to the content of the pseudo-crosslinking compound from 30:1 to 250:1, the invention attains an appropriate balance of a pressure-sensitive adhesive property, a cohesive property and a skin irritation, and also attains a skin sticking property, that is, a follow-up property at a sticking part.

Effect of the Invention

A composition of the invention has an appropriate pressure-sensitive adhesiveness, does not produce a glue residue when peeling off and furthermore has an excellent effect for a skin sticking property.

In addition, in a composition of the invention, one in which a content of a plasticizer is from 30 to 200 parts by weight relative to 100 parts by weight of an acrylic copolymer has effects that a skin irritation property is lower and the cohesive force is higher.

In addition, in a composition of the invention, as to one in which a content of a pseudo-crosslinking compound is from 0.3 to 10 parts by weight relative to 100 parts by weight of an acrylic copolymer, a high cohesive force is obtained by a pseudo-crosslinking property, and it has an effect that deterioration of a pressure-sensitive adhesive property can be avoided by a more appropriate crosslinking.

In addition, in a composition of the invention, one containing one or more from alkyl (meth) acrylate, hydroxyethyl (meth) acrylate and N-vinyl-2-pyrrolidone has an effect that a pressure-sensitive adhesiveness is particularly excellent.

In addition, in the invention, a composition, in which a cohesive force is particularly excellent and the problem of a glue residue is further favorably solved, can be provided by one in which alkyl (meth)acrylate is one or more consisting of an alcohol ester with an alkyl group of carbon numbers 4-12, a content thereof being from 30 to 80% by weight based on the entire copolymer, a content of hydroxyethyl (meth)acrylate is from 3 to 25% by weight based on the entire copolymer, and a content of N-vinyl-2-pyrrolidone is from 5 to 25% by weight based on the entire copolymer.

In addition, in the invention, a particularly excellent composition in the skin sticking property can be provided by one in which a shearing strain migration length (3 g, 2 min.) of a pressure-sensitive adhesive layer containing the composition is not more than a thickness of the pressure-sensitive adhesive layer, and a shearing strain migration length (80 g, 5 min.) is not less than 10 times of a thickness of the pressure-sensitive adhesive layer.

In the invention, a composition, in which the problem of a glue residue is further favorably solved, can be provided by one in which the pseudo-crosslinking compound is one or more from boric acid and/or salts thereof, an amine compound, an aluminate and a phenol compound.

A patch of the invention, which comprises a pressure-sensitive adhesive layer which contains any of the above-described pressure-sensitive adhesive compositions, and a backing, has an appropriate pressure-sensitive adhesiveness and an effect that a glue residue does not occur and a skin sticking property is excellent.

In the patch of the invention, a desirable effect to the skin can be performed by one containing a skin valuable.

In the patch of the invention containing a skin valuable, treatment of a skin disease and/or glamorization of the skin, removal of wrinkles, improvement of blood circulation and the like can be carried out effectively by one in which the skin valuable is a drug and/or a cosmetic material.

The acrylic copolymer in the composition of the invention contains hydroxyethyl (meth)acrylate from 3 to 25% by weight as a constituent. The content of said hydroxyethyl (meth) acrylate is 3-25%, preferably 7-20%.

In order to give a higher pressure-sensitive adhesive property, the acrylic copolymer in the composition of the invention contains alkyl (meth)acrylate, which consists of an ester with an alcohol of carbon numbers 4-12 of an alkyl group, from 30 to 80% by weight, preferably from 40 to 70% by weight. Examples include butyl (meth)acrylate, isobutyl (meth)acrylate, hexyl acrylate, octyl acrylate, 2-etylhexyl (meth)acrylate, isooctyl (meth)acrylate, dodecyl (meth)acrylate, and the like, while these may be used singly or in a combination. By making the content of alkyl (meth)acrylate not less than 30%, a higher pressure-sensitive adhesive property is attained, and by making it not more than 80%, a high cohesive force improvement by a pseudo-crosslinking which is a main aim of the invention is attained.

The content of hydroxyethyl (meth)acrylate is 3-25% as described above, preferably 7-20%. By making it not less than 3% by weight, the below-described pseudo-crosslinking property in a composition added with a plasticizer is high, giving a sufficient cohesive force to solve a glue residue when peeling off after sticking, and by making it not more than 25%, hardening of the copolymer is avoided to be able to obtain a sufficient pressure-sensitive adhesive property in the composition added with the plasticizer. If the content of the above-described N-vinyl-2-pyrrolidone in the copolymer is not less than 5% by weight, a glue residue does not occur when peeling off after sticking due to obtaining a sufficient cohesive force in a composition which is pseudo-crosslinked by adding a plasticizer, and if it is not more than 25% by weight, the copolymer does not harden; and therefore, a sufficient pressure-sensitive adhesive property can be obtained in the composition added with the plasticizer. Consequently, the content of N-vinyl-2-pyrrolidone in the copolymer is from 5 to 25% by weight, preferably from 10 to 20% by weight.

The above-described acrylic copolymer contains hydroxyethyl (meth)acrylate, which is in particular highly polar monomer, and N-vinyl-2-pyrrolidone in a high content, and thereby, it itself becomes a pressure-sensitive adhesive agent which is high in a cohesive force. In addition, as to the above-described acrylic copolymer, a polar monomer (for example, vinyl acetate, acrylamide, etc.), macromonomer and the like may be polymerized in the range from 1.0 to 40% by weight with an aim to further increase the cohesive force of a pressure-sensitive adhesive agent or to increase solubility of a drug or a cosmetic material in the pressure-sensitive adhesive agent.

In order to prepare the above-described acrylic copolymer, solution polymerization of a required monomer is carried out under presence of a polymerization initiator. However, a polymerization pattern is not limited to this. In addition, a polymerization condition is suitably selected mainly according to a kind of monomer. In case of carrying out the solution polymerization, for example, a designated amount of a required monomer is added with a general polymerization solvent such as ethyl acetate or the like, and may be reacted in a reaction vessel equipped with a stirring apparatus and a cooling-reflux apparatus under the presence of a polymerization initiator such as an azobis type or a peroxide type in an atmosphere of nitrogen at 70-90° C. for 8-40 hours. Further, the above-described monomer and the solvent may be poured in one time or suitably in portion wise. As for the polymerization initiator, the suitable portion-wise pouring is preferable according to the progress of a reaction.

As the above-described Azobis type polymerization initiator, illustrative are, for example, 2,2'-azobisisobutyronitrile, 1,1'-azobis(cyclohexane-1-carbonitrile), 2,2'-azobis-(2,4-dimethylvaleronitrile), and the like, and as the above-described peroxide type polymerization initiator, illustrative are, for example, lauroyl peroxide, benzoyl peroxide, di-tert-butyl peroxide, and the like.

In order to prepare the composition of the invention, a plasticizer is added to the above-described acrylic copolymer. The added amount of said plasticizer is preferably from 30 to 200 parts relative to 100 parts by weight of the acrylic copolymer. By making the added amount not less than 30 parts, a patch less in a skin irritation property can be obtained, and by making it not more than 200 parts, a higher cohesive force in a pressure-sensitive adhesive agent type by a pseudo-crosslinking described below can be obtained.

As the above-described plasticizer, illustrative are, for example, fatty acid esters of monovalent alcohols such as cetyl octanoate, hexyl laurate, isopropyl myristate, isopropyl palmitate, butyl stearate, myristyl lactate, and the like; dibasic acid esters such as dioctyl adipate, diethyl sebacate, dioctyl sebacate, dioctyl succinate, and the like; fatty acid esters of polyvalent alcohols and the like such as propylene glycol dicaprate, glycerol trioctanoate, glycerol tri(octanoate/decanoate), medium chain fatty acid triglyceride, and the like; and in particular, isopropyl myristate, isopropyl palmitate, diethyl sebacate, middle chain fatty acid triglyceride, and the like are preferably used.

The composition of the invention is characterized in that the composition is pseudo-crosslinked, wherein the plasticizer is added to the above-described acrylic copolymer, and further, a pseudo-crosslinking compound is added.

Since in case of increasing the content of the above-described pseudo-crosslinking compound, an augmentation effect of the cohesive force due to addition is easy to appear, and in case of decreasing it, the pressure-sensitive adhesiveness is improved, it is preferably from 0.3 to 10 parts relative to 100 parts of the acrylic copolymer, preferably from 0.5 to 5 parts.

In addition, the ratio of the content of the above-described plasticizer to the content of the above-described pseudo-crosslinking compound ranges from 30:1 to 250:1, preferably 30:1 to 200:1, more preferably 30:1 to 150:1, further preferably 30:1 to 120:1.

The pseudo-crosslinking compound in the invention is one or more selected from boric acid and/or a borate, an amine compound, an aluminate and a phenol compound.

As examples of the borate, illustrative are ammonium borate, triethyl borate, tributyl borate, isopropyl borate, potassium borate, calcium borate, barium borate, magnesium borate, triallyl borate, and the like. The borate can be an anhydrous compound or ahydrate. Ammonium borate octahydrate is in particular preferable. Boric acid is also in particular preferable.

As the amine compound, illustrative are monoamine compounds such as propylamine, diamine compounds such as hexanediamine and ethylenediamine, and triamine compounds such as diethylenetriamine. The diamine compounds are preferable, and hexanediamine and ethylenediamine are particularly preferable.

As the amine compound, illustrative are monoamine compounds such as propylamine, diamine compounds such as hexanediamine and ethylenediamine, and triamine compounds such as diethylenetriamine. The diamine compounds are preferable, and hexanediamine and ethylenediamine are particularly preferable.

As the aluminate, illustrative are potassium aluminate, sodium aluminate, calcium aluminate, magnesium aluminate, and the like. Sodium aluminate is particularly preferable.

As the phenol compound, illustrative are, except phenol, benzene diols such as pyrocatechol, resorcinol, and hydroquinone. The benzene diols are preferable, and resorcinol is particularly preferable.

The added amount of the pseudo-crosslinking compound is preferably from 0.3 to 10 parts relative to 100 parts of the acrylic copolymer, preferably from 0.5 to 5 parts. By making it not less than 0.5 parts by weight, a higher cohesive force can be obtained due to a pseudo-crosslinking property, and by making it not more than 10 parts by weight, a preferable crosslinking is obtained to avoid deterioration of the pressure-sensitive adhesive property.

The pseudo-crosslinking in the invention is to try augmentation of the cohesive force by interactions such as hydrogen bonding, electrostatic interaction, van der Waals force, and the like between a hydroxyl group in the acrylic copolymer and the pseudo-crosslinking compound such as boric acid (salts), the amine compound, the aluminate, the phenol compound, and the like, a loose bonding between copolymers through the pseudo-crosslinking compound. The pseudo-crosslinking is micro-structurally different from a rigid crosslinking due to conventionally known chemical or ionic bondings, and in the case of the pseudo-crosslinking a composition does not produce gel. The composition after crosslinking by the invention is soluble in a favorable solvent and hardly produces insoluble fractions (gel fractions). This is obviously different from a conventional crosslinking.

The difference of physical properties between a conventional crosslinking pressure-sensitive adhesive agent and the pseudo-crosslinking pressure-sensitive adhesive agent of the invention can clearly be differentiated in a creep behavior. A pressure-sensitive adhesive agent with a chemical crosslinking or an ionic crosslinking behaves like rubber without losing elasticity even under a relatively high stress. On the contrary, a pressure-sensitive adhesive agent with a pseudo-crosslinking behaves elastically under a low stress; however, it behaves plastically under a medium stress, destroying the pseudo-crosslinking. As shown in FIG. 1 schematically, a tape coated on one side of a backing with composition (A) chemically crosslinked with polyisocyanate or the like, wherein 50 parts of the plasticizer was added to 100 parts of the acrylic copolymer, the composition (B) pseudo-crosslinked with boric acid, wherein 50 parts of the plasticizer was added to 100 parts of the acrylic copolymer, and the composition (C) in which 50 parts of the plasticizer was added to 100 parts of the acrylic copolymer only, were stuck on a Bakelite board in the area of 1 cm$^2$, and the shearing strain behaviors are shown when applying 3.0 g of weighting and 8.0 g of weighting. The behaviors of the pseudo-crosslinking pressure-sensitive adhesive agent for weighting of 3.0 g and 80 g are clearly different from those of the non-crosslinking pressure-sensitive adhesive agent and the chemical-crosslinking pressure-sensitive adhesive agent.

In the above test, a shearing strain migration length after 2 min. under weighting of 3 g (this length is referred as "shearing strain migration length (3 g, 2 min.))" is an indicator of elasticity under the above low stress, and a shearing strain migration length after 5 min. under weighting of 80 g (this length is referred as "shearing strain migration length (80 g, 5 min.))" is an indicator of elasticity under the above medium stress. Therefore, the composition and the patch containing the composition of the invention are rich in elasticity under a low stress and in plasticity under a medium stress. Among compositions of the invention and tapes (patches) containing the compositions, one, in which "shearing strain migration length (3 g, 2 min.)" is not more than the thickness of the pressure-sensitive adhesive layer and also "shearing strain migration length (80 g, 5 min.)" is not less than ten times of the thickness of the pressure-sensitive adhesive layer, is preferable.

As described above, one of the characteristics of the composition of the invention is reduction of a skin irritation property against a non-crosslinking preparation and improvement of a skin sticking property against a chemically crosslinking preparation. In addition, the chemical-crosslinking preparation can not follow up movement of the skin when sticking to the skin and a pressure-sensitive adhesive tape (a patch) often peels off, while the patch of the invention can follow up a shape change of the skin by a plastic change of the pressure-sensitive adhesive base; and therefore, a skin sticking property is far excellent. Further, the composition and the patch of the invention are also excellent in a shape-keeping property.

Although the patch of the invention constitutes lamination of the above-described acrylic composition layer on one side of a backing, further it can be made a transdermal absorption preparation or a patch type cosmetic preparation by addition of a skin valuable.

The above-described backing is preferably one which is non-permeable or scarcely permeable for a drug and soft, illustrative are, for example, resin films such as polyethylene, polypropylene, ethylene-methyl acrylate copolymer, ethylene-vinyl acetate copolymer, polyvinylidene chloride, polyurethane, nylon, polyethylene terephthalate, polybutylene terephthalate, and the like; aluminum sheet and the like, and may be a laminated sheet of these or may be laminated with a woven fabric or a non-woven fabric. In addition, to increase a sticking property with the pressure-sensitive adhesive layer, a surface treatment such as corona treatment, plasma discharge treatment, or the like may be operated, or anchor coating treatment by a anchor agent may be operated.

The drug as a skin valuable contained in the above-described composition is not particularly limited as long as it can transdermally permeate a biomembrane; illustrative are, for example, antipyretic-analgesic agents, steroidal anti-inflammatory agents, vasodilators, antiarrythmic agents, hypotensors, local anesthetics, hormonal agents, anti-histaminic agents, general anesthetics, hypnotic-sedatives, anti-epileptic agents, psychoneurotic agents, skeletal muscle relaxants, agents for the autonomic nervous system, anti Parkinsonism agents, diuretics, vasoconstrictors, respiratory stimulants, narcotics, and the like.

As the above-described antipyretic-analgesic agents, illustrative are, for example, ibuprofen, naproxen, flurbiprofen, ketoprofen, sodium amfenac, and the like; as the above-described steroidal anti-inflammatory agents, illustrative are, for example, hydrocortisone, tramcinolone, dexamethasone, betamethasone, prednisolone, and the like.

As the above-described vasodilators, illustrative are, for example, diltiazem hydrochloride, pentaerythritol tetranitrate, isosorbide nitrate, and the like. As the above-described antiarrythmic agents, illustrative are, for example, procainamide hydrochloride, disopyramide, mexiletine hydrochloride, and the like. As the above-described hypotensors, illustrative are, for example, clonidine hydrochloride, bunitrolol hydrochloride, captopril, and the like. As the above-described local anesthetics, illustrative are, for example, ethyl aminobenzoate, teracaine hydrochloride, procaine hydrochloride, dibucaine hydrochloride, oxybuprocaine hydrochloride, propitocaine hydrochloride, and the like. As the above-described hormonal agents, illustrative are, for example, propylthiouracil, thiamazole, metenolone acetate, estradiol, estriol, progesterone, and the like. As the above-described antihistamines, illustrative are, for example, diphenhydramine hydrochloride, chlorpheniramine maleate, promethazine, cyproheptadine hydrochloride, diphenylpyraline hydrochloride, and the like.

As the above-described general anesthetics, illustrative are, for example, thiopental sodium, pentobarbital sodium, and the like. As the above-described hypnotic-sedatives, illustrative are, for example, bromovalerylurea, amobarbital, phenobarbital, and the like. As the above-described anti-epileptic agents, illustrative are, for example, phenytoin sodium, and the like.

As the above-described psycho neuro agents, illustrative are, for example, chlorpromazine hydrochloride, thioridazine, meprobamate, imipramine hydrochloride, chlordiazepoxide, diazepam, and the like. As the above-described skeletal muscle relaxants, illustrative are, for example, suxamethonium hydrochloride, eperisone hydrochloride, and the like. As the above-described agents for the autonomic nervous system, illustrative are, for example, neostigmine bromide, bethanechol chloride, and the like. As the above-described anti Parkinsonism agents, illustrative are, for example, amantadine hydrochloride, and the like. As the above-described diuretics, illustrative are, for example, hydroflumethiazide, isosorbide, FUROSEMIDE GR (4-chloro-2-(furan-2-ylm ethylamino)-5-sulfamoylbenzoic acid; DepoMed, Inc. Menlo Park Calif.), and the like.

As the above-described vasoconstrictors, illustrative are, for example, phenylephrine hydrochloride, and the like. As the above-described respiratory stimulants, illustrative are, for example, lobeline hydrochloride, dimorpholamine, naloxone hydrochloride, and the like. As the above-described narcotics, illustrative are, for example, morphine hydrochloride, codeine phosphate, cocaine hydrochloride, pethidine hydrochloride, and the like.

Specific examples of cosmetic material as a skin valuable are listed in the following; skin-whitening ingredients such as ascorbil palmitate, kojic acid, rucinol, tranexamic acid, oil-soluble glycyrrhiza extract, and a vitamin A derivative, anti-wrinkle ingredients such as retinol, retinoic acid, retinol acetate, and retinol palmitate, circulation promoting ingredients such as tocopherol acetate, capsaicin, vanillylamide nonylate, diet ingredients such as raspberry ketone, evening primrose extract, and seaweed extract, antibacterial ingredients such as isopropyl-methylphenol, sensitizing agent, and zinc oxide, and vitamins such as vitamin $D_2$, vitamin $D_3$, and vitamin K are included in particular preferably.

Although the content of the above-described drug or cosmetic material is appropriately determined according to the kind and use purpose, by making it much the efficacy can be increased and by making it little the pressure-sensitive adhesive property can be increased. Therefore, the content of the above-described drug or cosmetic material is preferably from 0.01 to 50% by weight in the pressure-sensitive adhesive layer. Even if the drug exists under a supersaturation state in the pressure-sensitive adhesive layer, or under a deposition state of crystals, there is in particular no problem. In addition, the drug may be capsuled with a absorption promoter, or a drug reservoir layer may be provided.

Although the thickness of the pressure-sensitive adhesive layer in the patch of the invention is not particularly limited, by making it thick an added amount of the skin valuable can be reduced to keep a pressure-sensitive adhesiveness, and by making it thin, diffusion of the skin valuable, which exists in the pressure-sensitive adhesive layer near the backing, to a surface of the pressure-sensitive adhesive layer becomes easy to increase a drug release ratio. Therefore, the thickness of the pressure-sensitive adhesive layer is preferably 10-200 µm.

For preparation of a transdermal absorption preparation of the invention, a preparation method of a conventionally known pressure-sensitive adhesive tape (patch) can be used. For example, in a solvent coating method, the pressure-sensitive adhesive agent, the plasticizer, the pseudo-crosslinking compound and the skin valuable of a designated amount are dissolved or dispersed in solvent such as ethyl acetate, and a method to coat and dry an obtained liquid on a backing, a method to coat and dry it on a release paper and then to transfer it on a backing, and the like are preferably used.

BRIEF DESCRIPTION OF THE DRAWINGS

FIG. 1 is the schematic FIGURE in which the creep behavior in the chemical crosslinking state, pseudo-crosslinking state or non-crosslinking states of the acrylic copolymer added with the plasticizer is different (the numeral in ( ) is the load.).

DESCRIPTION OF SYMBOLS

A; Chemical crosslinking
B: Pseudo-crosslinking
C: Non-crosslinking

BEST EMBODIMENT FOR CARRYING OUT THE INVENTION

In the following, the invention is explained in more detail by examples; however, it is not limited to these. Further, in the following, "part" means "part by weight".

Syntheses of Acrylic Copolymers

Example 1

2-Ethylhexyl acrylate 300 parts, hydroxyethyl acrylate 50 parts, N-vinyl-2-pyrrolidone 50 parts and ethyl acetate 300 parts were placed in a separable flask with a stirring apparatus and a reflux-cooling apparatus, and warmed to 75° C. under stirring and replacing with nitrogen. Benzoyl peroxide 2 parts was dissolved in ethyl acetate 20 parts; the solution was divided in 5 portions; one portion among these was added to the separable flask, and polymerization started. From 2 hours after the initiation of the reaction, the remaining 4 portions was added at every 1 hour interval, and the reaction was continued further for 2 hours. Further, after the initiation of the reaction, ethyl acetate was added 4 times at every 2 hours interval in every 50 parts to adjust a viscosity. After the reaction, the mixture was cooled, followed by addition of ethyl acetate to obtain a pressure-sensitive adhesive agent's solution of solid-part concentration 30% by weight.

Example 2

Except making the monomer composition in Example 1 butyl acrylate 300 parts, hydroxyethyl acrylate 60 parts and N-vinyl-2-pyrrolidone 40 parts, all was made in the same way to obtain a pressure-sensitive adhesive agent's solution of solid-part concentration 30% by weight.

Example 3

Except a change that the monomer composition in Example 1 became 2-ethylhexyl acrylate 300 parts, hydroxyethyl acrylate 60 parts , N-vinyl-2-pyrrolidone 30 parts and ethyl acetate 50 parts, and the initiator was azobisisobutylnitrile in stead of benzoyl peroxide, all was made in the same way to obtain a pressure-sensitive adhesive agent's solution of solid-part concentration 30% by weight.

Comparative Example 1

Except that the monomer composition in Example 1 was 2-ethylhexyl acrylate 300 parts, hydroxyethyl acrylate 5 parts and N-vinyl-2-pyrrolidone 80 parts, all was made in the same way to obtain a pressure-sensitive adhesive agent's solution of solid-part concentration 30% by weight.

Preparation of Test Sheet and Measurement of Shearing Strain Migration Length (1)

The pressure-sensitive adhesive agent's solution obtained in Examples 1, 2 or 3, or the comparative example 1 was added with a plasticizer and a pseudo-crosslinking compound, and the all the liquid was stirred homogeneously by a dissolver to obtain a mix liquid. The obtained mix liquid was coated on a PET film of thickness 35 µm, which is treated with silicon, so that the thickness of the pressure-sensitive adhesive agent after drying became 100 µm, and dried, and then, the above-described pressure-sensitive adhesive agent was laminated on the PET film of thickness 35 µm to obtain a pressure-sensitive adhesive sheet for the skin. Then, the prepared sheet was cut in width 1 cm as a tape form, and after it was adhered closely on a Bakelite board in the sticking area of 1 cm×1 cm by at 25° C. by shuttling a roller of load 500 g, the board was placed vertically to measure a shearing strain migration length (3 g, 2 min.) and a shearing strain migration length (8 g, 5 min.)

In Table 1 in the following, the compositions of the pressure-sensitive adhesive sheets for the skin and the measurement results of shearing strain migration length, which were prepared and measured above, are shown as the examples. In Table 2, as the comparative examples, the results prepared and measured according to the examples are shown. Further, as to the pseudo-crosslinking compounds, each of a reagent special grade was used.

TABLE 1

| Example | Acrylic copolymer solid part (weight ratio) | Plasticizer (weight ratio) | Pseudo-crosslinking compound (weight ratio) | Shearing strain migration length (mm) (3 g, 2 min.) | Shearing strain migration length (mm) (80 g, 5 min.) |
|---|---|---|---|---|---|
| 4 | Example 1 (100) | IPM (50) | Boric acid (1.0) | 0 | $\geq 2$ |
| 5 | Example 1 (100) | IPP (60) | Boric acid (1.5) | 0 | $\geq 2$ |
| 7 | Example 2 (100) | Diethyl sebacate (60) | Ammonium borate octahydrate (1.8) | 0 | $\geq 2$ |

TABLE 2

| Comparative example | Acrylic copolymer solid part (weight ratio) | Plasticizer (weight ratio) | Pseudo-crosslinking compound (weight ratio) | Shearing strain migration length (mm) (3 g, 2 min.) | Shearing strain migration length (mm) (80 g, 5 min.) |
|---|---|---|---|---|---|
| 2 | Example 1 (100) | IPM (10) | Boric acid (1.5) | 0 | 0 |
| 3 | Example 1 (100) | IPP (250) | Boric acid (1.5) | $\geq 2$ | $\geq 2$ |
| 4 | Example 2 (100) | Myrystyl lactate (50) | None | $\geq 2$ | $\geq 2$ |
| 5 | Example 3 (100) | None | None | 0 | 0 |
| 6 | Comparative example 1 (100) | Myrystyl lactate (60) | Boric acid (1.5) | 0.5 | $\geq 2$ |

In Table 3, the measurement values in the chemical crosslinking and the ionic crosslinking. As the chemical crosslinking agents CORONATE HL (trimethyl propane/hexamethylene diisocyanate (trimeric adduct); Nippon Polyurethane Industry Co., Ltd. Tokyo, Japan; manufactured by Nihon Polyurethane) and aluminum acetylacetonate (reagent special grade) were used.

TABLE 3

| Comparative example | Acrylic copolymer solid part (weight ratio) | Plasticizer (weight ratio) | Crosslinking agent (weight ratio) | Shearing strain migration length (mm) (3 g, 2 min.) | Shearing strain migration length (mm) (80 g, 5 min.) |
|---|---|---|---|---|---|
| 7 | Example 1 (100) | IPM (50) | CORONATE HL (1.0) | 0 | 0.6 |
| 8 | Example 1 (100) | Myrystyl lactate (70) | Aluminum acetylacetonate (0.7) | 0 | 0.4 |

Measurement of Gel Percentage

Each sheet prepared as described above was cut in 20 cm$^2$, and the weight of the pressure-sensitive adhesive layer (W1) was measured. Then, the sheet was immersed in ethyl acetate and let it stand for 3 days to extract a solvent soluble part. After that, the insoluble part was taken out, dried and followed by measurement of the weight of the pressure-sensitive adhesive layer (W2) to calculate a gel percentage by the below equation. The results are shown in Table 4.

$$(W2 \times 100)/(W1 \times A/B)$$

A: (pressure-sensitive adhesive agent+crosslinking agent) weight, B: (pressure-sensitive adhesive agent+plasticizer+crosslinking agent) weight

TABLE 4

|  | Acrylic copolymer composition | Gel percentage (%) |
|---|---|---|
| Example 8 | Example 4 | 0.0 |
| Example 9 | Example 5 | 0.0 |
| Example 11 | Example 7 | 0.0 |
| Comparative example 9 | Comparative example 7 | 47 |
| Comparative example 10 | Comparative example 8 | 32 |

Skin Irritation Test and Sticking Property Test (Skin Irritation)

As for the above-obtained test sheet, the following evaluation was carried out, and the results are shown in Table 5. Each test sheet (20 cm$^2$) was stuck on upper arm parts of five adult males, and peeled off after 24 hours. A skin condition after 1 hour from peeling off was observed by visual inspection, and evaluated according to the below evaluation standard to make the mean value of the total sum of evaluation points of 5 persons the index number.

(Evaluation Standard)

0: No erythema, 1: Very slight erythema in a barely detectable degree, 2: Apparent erythema, 3: erythema in a medium degree, 4: Strong erythema with a deep red color Sticking Property Each transdermal absorption preparation was stuck on upper arm parts of five adult males, and peeled off after 24 hours. A sticking condition of the sheet on the skin just before peeling off was observed by visual inspection, and evaluated according to the below evaluation standard.

(Evaluation Standard)

◯: Complete sticking for almost all members, Δ: Partial peeling off for 1-3 persons, ×: peeling off for 4-5 persons (Glue Residue Property)

Each transdermal absorption preparation was stuck on upper arm parts of five adult males, and peeled off after 24 hours. A sticking condition of the sheet on the skin just after peeling off was observed by visual inspection, and evaluated according to the below evaluation standard.

(Evaluation Standard)

◯: No glue residue for almost all members, Δ: Partial glue residue for 1-3 persons, ×: Glue residue for 4-5 persons

TABLE 5

|  | Acrylic copolymer | Irritation property | Sticking property | Glue residue property |
|---|---|---|---|---|
| Example 12 | Example 4 | 0.4 | ◯ | ◯ |
| Example 13 | Example 5 | 0.6 | ◯ | ◯ |
| Example 14 | Example 7 | 0.6 | ◯ | ◯ |
| Comparative example 11 | Comparative example 7 | 0.4 | Δ | ◯ |
| Comparative example 12 | Comparative example 8 | 0.8 | X | ◯ |

Preparation and Evaluation of Transdermal Absorption Preparation and Cosmetic Patch Except blending the alkyl acrylate composition containing the Examples 4 or 5, or the comparative examples 4 or 5 as a constituent and the skin valuable as shown in Table 6, a medicinal patch or a cosmetic patch was prepared and evaluated in the same way described above. The results are shown in Table 6. In the table, H is indomethcin, K is ketoprofen, and E is vitamin E respectively.

Irritation Property

A test piece (2.5×2.5 cm) of the tape preparation was stuck on a shaven back of a Japanese White rabbit and peeled off after 24 hours. A skin erythema condition after 1 hour from peeling off was observed by visual inspection. Further, in the test, the formation of edema and incrustation was not detected. Each preparation was stuck to 4 rabbits in total. The degree of rash erythema was evaluated according to the below evaluation standard by 5 steps of 0-4. O: no erythema, 1: very slight erythema in a barely detectable degree, 2: apparent erythema, 3: erythema in a medium degree, 4: strong erythema with a deep red color. The mean value of the total sum of an evaluation point in each rabbit, which was divided by 4, was made a skin irritation index number of each tape preparation.

Sticking Property

In the same operation as the above irritation property test, the tape preparation was stuck to a rabbit skin, and the presence or absence of the sticking property just before peeling off was observed by visual inspection. The evaluation standard is as follows.

0: No peeling off of preparation; 1: Partial peeling off is detected; 2: Apparent peeling off is detected The mean value (a value in which the total sum of an evaluation point was divided by 4) was made a sticking property index number of each tape preparation.

TABLE 6

| | Acrylic copolymer | Skin valuable (added amount %) | Irritation property | Sticking property |
|---|---|---|---|---|
| Example 16 | Example 4 | E (5) | 0.75 | 0.25 |
| Example 17 | Example 5 | H (5) | 0.5 | 0.25 |
| Comparative example 13 | Comparative example 4 | K (5) | 3.0 | 0.25 |
| Comparative example 14 | Comparative example 5 | E (5) | 2.25 | 1.75 |

Example 18

2-Ethylhexyl acrylate 300 parts, hydroxyethyl acrylate 50 parts, N-vinyl-2-pyrrolidone 30 parts and ethyl acetate 300 parts were placed in a separable flask with a stirring apparatus and a reflux-cooling apparatus, and warmed to 75° C. under stirring and replacing with nitrogen. Benzoyl peroxide 2 parts was dissolved in ethyl acetate 20 parts; the solution was divided in 5 portions; one portion among these was added to the separable flask, and polymerization started. From 2 hours after the initiation of the reaction, the remaining 4 portions was added at every 1 hour interval, and the reaction was continued further for 2 hours. Further, after the initiation of the reaction, ethyl acetate was added 4 times at every 2 hours interval in every 50 parts to adjust a viscosity. After the reaction, the mixture was cooled, followed by addition of ethyl acetate to obtain a pressure-sensitive adhesive agent's solution of solid-part concentration 30% by weight and viscosity $1.2 \times 10^4$ cps.

Example 19

Except making the monomer composition in Example 18 2-ethylhexyl acrylate 300 parts, hydroxyethyl acrylate 50 parts, acrylic acid 20 parts and N-vinyl-2-pyrrolidone 80 parts, all was made in the same way to obtain a pressure-sensitive adhesive agent's solution of solid-part concentration 30% by weight and viscosity $1.8 \times 10^4$ cps.

Comparative Example 15

Except that the monomer composition in Example 18 was 2-ethylhexyl acrylate 300 parts, hydroxyethyl acrylate 10 parts, acrylic acid 3 parts and N-vinyl-2-pyrrolidone 80 parts, all was made in the same way to obtain a pressure-sensitive adhesive agent's solution of solid-part concentration 30% by weight and viscosity $1.5 \times 10^4$ cps.

Preparation of Test Sheet and Measurement of Shearing Strain Migration Length (2)

The pressure-sensitive adhesive agent's solution obtained in Example 18 or 19, or the comparative example 15 was added with a plasticizer and a pseudo-crosslinking compound, and the all the liquid was stirred homogeneously by a dissolver to obtain a mix liquid. The obtained mix liquid was coated on a PET film of thickness 35 μm, which is treated with silicon, so that the thickness of the pressure-sensitive adhesive agent after drying became 100 μm, and dried, and then, the above-described pressure-sensitive adhesive agent was laminated on the PET film of thickness 35 μm to obtain a pressure-sensitive adhesive sheet for the skin (patch). Then, the prepared sheet was cut in width 1 cm as a tape form, and after it was adhered closely on a Bakelite board in the sticking area of 1 cm×1 cm by at 25° C. by shuttling a roller of load 500 g, the board was placed vertically to measure a shearing strain migration length (3 g, 2 min.) and a shearing strain migration length (8 g, 5 min.).

In Table 7 described below, the compositions and the measurement results of shearing strain migration length of the pressure-sensitive adhesive sheets for the skin (patches), which were prepared and measured above, are shown as the examples. In Table 8, as the comparative examples, the results prepared and measured according to the examples are shown. Further, as to the pseudo-crosslinking compounds, each of a reagent special grade was used. In practical blending, oxo acid was added in a designated amount as 5% aqueous solution. A case in which the shearing strain migration length is more than 2 mm was made >2. Other pseudo-crosslinking compounds were added in a designated amount as 5% tetrahydrofuran solution.

TABLE 7

| | Acrylic copolymer solid part | Plasticizer | Pseudo-crosslinking | Shearing strain migration length (mm) | |
|---|---|---|---|---|---|
| Example | (weight ratio) | (weight ratio) | compound (weight ratio) | (3 g, 2 min.) | (80 g, 5 min.) |
| 20 | Example 18 (100) | IPP (60) | Sodium aluminate (0.5) | 0 | ≧2 |
| 21 | Example 18 (100) | Myrystyl lactate (70) | Resorcinol (0.7) | 0 | ≧2 |
| 22 | Example 19 (100) | IPP (80) | Ammonium borate octahydrate (2.0) | 0 | ≧2 |

TABLE 8

| Comparative example | Acrylic copolymer solid part (weight ratio) | Plasticizer (weight ratio) | Pseudo-crosslinking compound (weight ratio) | Shearing strain migration length (mm) (3 g, 2 min.) | (80 g, 5 min.) |
|---|---|---|---|---|---|
| 16 | Example 18 (100) | IPM (10) | Boric acid (1.0) | 0 | 0 |
| 17 | Example 18 (100) | IPP (250) | Sodium aluminate (2.0) | 1.5 | ≧2 |
| 18 | Example 19 (100) | Myrystyl lactate (50) | None | ≧2 | ≧2 |
| 19 | Comparative example 15 (100) | Myrystyl lactate (60) | Hexanediamine (1.0) | 0.5 | ≧2 |
| 20 | Comparative example 15 (100) | IPM (60) | Sodium aluminate (2.0) | 1.0 | ≧2 |

INDUSTRIAL APPLICABILITY

Since the composition and the patch (transdermal absorption preparation, cosmetic sheet) using it is the constitution as described above, a favorable sticking property with well-balanced pressure-sensitive adhesiveness and cohesive force is shown; and therefore, when peeling off there is no glue residue, and a skin irritation due to a mechanical irritation and the like such as injury of a keratin layer of a skin surface and hair plucking can be reduced. Consequently, the invention greatly contributes to the development of patch production industries and the related industries.

The invention claimed is:

1. A patch comprising a pressure-sensitive adhesive layer comprising an acrylic copolymer containing from 3 to 25% by weight of hydroxyethyl (meth)acrylate as a constituent, a plasticizer and a pseudo-crosslinking compound, wherein the pseudo-crosslinking compound is one or more compounds selected from the group consisting of hexanediamine, ethylenediamine, diethylenetriamine, potassium aluminate, sodium aluminate, calcium aluminate, resorcinol and hydroquinone, and the ratio of the content of the plasticizer to the content of the pseudo-crosslinking compound ranges from 30:1 to 150:1.

2. The patch according to claim 1, wherein a content of the plasticizer is from 30 to 200 parts by weight relative to 100 parts by weight of an acrylic copolymer.

3. The patch according to claim 1, wherein a content of the pseudo-crosslinking compound is from 0.3 to 10 parts by weight relative to 100 parts by weight of the acrylic copolymer.

4. The patch according to claim 1, wherein the acrylic copolymer is a copolymer comprising alkyl (meth)acrylate, hydroxyethyl (meth)acrylate and N-vinyl-2-pyrrolidone.

5. The patch according to claim 4, wherein a content of alkyl (meth)acrylate is from 30 to 80% by weight based on the entire copolymer, a content of hydroxyethyl (meth)acrylate is from 3 to 25% by weight based on the entire copolymer, and a content of N-vinyl-2-pyrrolidone is from 5 to 25% by weight based on the entire copolymer, and the alkyl (meth)acrylate is an alcohol ester with an alkyl group of carbon numbers 4-12.

6. The patch according to claim 1 further comprising a backing.

7. The patch according to claim 6 comprising a skin valuable.

8. The patch according to claim 7, wherein the skin valuable is a drug and/or a cosmetic material.

9. The patch according to claim 1, wherein the hydroxy group in the acrylic polymer and the pseudo-crosslinking compound are bound by hydrogen bonding or van der Waals force so that a psuedo-crosslink is formed between copolymers.

10. The patch according to claim 1 wherein the plasticizer is one or more compound selected from the group consisting of isopropyl myristate, myristyl lactate and diethyl sebacate.

11. The patch according to claim 1, wherein a content of the plasticizer is from 30 to 200 parts by weight relative to 100 parts by weight of an acrylic copolymer, and a content of the pseudo-crosslinking compound is from 0.3 to 10 parts by weight relative to 100 parts by weight of the acrylic copolymer.

12. The patch according to claim 1, wherein the ratio of the content of the plasticizer to the content of the pseudo-crosslinking compound ranges from 30:1 to 120:1.

13. The patch according to claim 12, wherein a content of the plasticizer is from 30 to 200 parts by weight relative to 100 parts by weights of an acrylic copolymer, and a content of the pseudo-crosslinking compound is from 0.3 to 10 parts by weight relative to 100 parts by weight of the acrylic copolymer.

14. The patch according to claim 1, wherein the plasticizer is myristyl lactate.

* * * * *